United States Patent [19]

Törnblom

[11] Patent Number: 4,703,265
[45] Date of Patent: Oct. 27, 1987

[54] METHOD AND APPARATUS FOR COMPENSATING FOR DIFFERENT DEPTHS OF SUN CURRENTS INDUCED IN THE OBJECT TESTED FOR IMPERFECTIONS

[75] Inventor: Bengt H. Törnblom, Västerås, Sweden

[73] Assignee: Törnbloms Kvalitetskontroll AB, Sweden

[21] Appl. No.: 702,314

[22] Filed: Feb. 15, 1985

[30] Foreign Application Priority Data

Feb. 17, 1984 [SE] Sweden ............................ 8400861

[51] Int. Cl.$^4$ ................. G01N 27/90; G01R 33/12
[52] U.S. Cl. ........................... 324/232; 324/225
[58] Field of Search ............ 324/225, 227, 232, 233, 324/238, 240

[56] References Cited

U.S. PATENT DOCUMENTS

| | | | |
|---|---|---|---|
| 4,237,419 | 12/1980 | Tornblom et al. | 324/232 X |
| 4,303,885 | 12/1981 | Davis et al. | 324/232 X |
| 4,326,166 | 4/1982 | Pigeon et al. | 324/225 |
| 4,503,392 | 3/1985 | Fastritsky et al. | 324/232 |

FOREIGN PATENT DOCUMENTS

| | | | |
|---|---|---|---|
| 2082330 | 3/1982 | United Kingdom | 324/225 |
| 0871056 | 10/1981 | U.S.S.R. | 324/230 |
| 0905765 | 2/1982 | U.S.S.R. | 324/232 |
| 1046724 | 10/1983 | U.S.S.R. | 324/232 |

OTHER PUBLICATIONS

Kiev Light Ind, "Double-Frequency Modulation Defectoscope . . . " Instrument, Measuring and Testing, p. 54, Derwent Abstract E9739E/17.

Primary Examiner—Gerard R. Strecker
Attorney, Agent, or Firm—Watson Cole et al.

[57] ABSTRACT

A method for testing an electrically conductive test object with regard to an imperfection therein uses a transducer supplied with drive signals of two different frequencies so that via inductive coupling between the transducer and the test object, signal information is received from the transducer which can be processed to indicate the presence of an imperfection. The invention is characterized in that the transducer is designed and supplied with drive signals in such wise that the effect of the different depth penetration of currents induced in the test object at the two frequencies can be compensated for.

15 Claims, 4 Drawing Figures

METHOD AND APPARATUS FOR COMPENSATING FOR DIFFERENT DEPTHS OF SUN CURRENTS INDUCED IN THE OBJECT TESTED FOR IMPERFECTIONS

TECHNICAL FIELD

This invention relates to the general field of testing electrically conducting bodies using an electrical transducer to measure currents induced in the test body and to determine the presence of imperfections (e.g. cracks) in the body.

A problem in connection with, for example, crack detection by means of an eddy current technique—which problem is often overlooked—is the disturbing influence of the surrounding surface structure of the object under test on the measurement result, which in many cases can drastically downgrade the accuracy of the measurement result. In, for example, crack detection of hot extruded objects, for example slabs, oscillation marks (OSCM) on the surface of the object often constitute a very disturbing and measurement-limiting factor, in spite of the fact that these marks are relatively harmless to the quality of the end product.

DISCUSSION OF PRIOR ART

This undesired influence of, for example, oscillation marks cannot be efficiently suppressed when using known multi-frequency methods based on so-called "small signal theories", that is, methods which utiilize the differential coefficient of a function at a certain point to emphasize or suppress a variable. The reason for this is that these methods have very limited lift-off (LO) operating ranges, for example.

Known devices and methods, which exhibit these limitations, are for example the method described by Hugo L. Libby in "Introduction to Electromagnetic Nondestructive Test Methods", published in 1979 by Robert E. Kriger Publishing Co. (New York), U.S. Pat. No. 4,303,885 and others. The copending Swedish patent application No. 8400698-0 entitled "Dynamic Transformation" corresponds to U.S. application Ser. No. 699,594, now U.S. Pat. No. 4,661,777, however, describes an electronic solution to the small signal problem.

One object of the present invention is to provide a solution to the problems mentioned above and other problems associated therewith. A further object of the invention is to constitute an alternative and/or a complement to the testing method described in the above-mentioned Swedish patent application.

Since the invention primarily relates to the transducer, it can be considered to relate to a transducer optimization, whereas the above-mentioned Swedish patent application entitled "Dynamic Transformation" can be considered to relate to an electronic optimization of the measurement/testing equipment. The total effect of both these kinds of optimizations provides excellent conditions for suppressing undesired influences on the measurement result from changes, which may be relatively harmless per se, such as OSCM and LO-variations.

Swedish patent application No. 8302738-3 describes the reasons for, and the need of, utilizing high (H) and low (L) carrier frequencies which differ considerably from each other, for example $H/L > 10$. This means that the difference in the depth of penetration ($\Delta DJ$) increases for the eddy currents induced in the test object. The consequence of this, of course, is also that the undesired effects of the difference in the depth of penetration will likewise increase markedly, thus, for example, deteriorating the signal-to-noise ratio (S/N) of the measurement result.

The invention relates to a method as well as a device for overcoming these problems, and the following description should be understood as describing both these features although only one of them is discussed in detail in the following text.

DEFINITIONS

Some definitions and clarifications, which are important to an understanding of the present invention, will be clear from the following.

The term TRANSDUCER is intended to cover, for example, a magnetic flux-generating part and a magnetic flux-sensing part, consisting of a wire loop or a coil or an arrangement of these or similar elements. The transducer may also consist of a primary coil supplied with current and a sensing secondary coil. In those cases where the flux is generated by other equipment, the transducer may also consist of only a flux-sensing part.

By the term TEST OBJECT is meant, for example, a billet, a sheet, a tube, a wire and a profiled material of any cross-sectional shape.

By the term IMPERFECTION is meant, not only a defect, a crack, a pore, a flake and a hole, but also dimensional changes and other types of imperfections in the test object.

By the term FREQUENCY is usually meant the frequency (carrier frequency) or frequency component with which the transducer is supplied. However, in certain cases the term also comprises a complex of frequencies, for example a complex dominated by a certain frequency.

By the terms LIFT-OFF and LO are normally meant the distance between the mid-point (MPKT) of the transducer and the sum current ($\Sigma I$) in the test object. This distance may vary as a function of the frequency to which it refers, but it may also be constant as will be clear from the following.

By H is meant the higher of two frequencies or a signal derived from or dominated by the higher frequency.

By L is meant the lower of two frequencies or a signal derived from or dominated by the lower frequency.

By the term SUM CURRENT ($\Sigma I$) is meant, for example, the imaginary current in the test object which would give rise to the total effect of the partial currents in the test object. The sum current is normally different for different frequencies. Sum currents of different frequencies extend to different depths in the test object.

By the term MID-POINT (MPKT) of the transducer, is meant, for example, the imaginary point in the transducer to which the coupling or interaction between the transducer and the sum current ($\Sigma I$) can be considered to relate in order for the effect to be the same as the sum effect of the coupling between sum current and the resoective partial element in the transducer. This mid-point is often different for different frequencies. By mid-point can also be meant, for example, a single wire loop with a function corresponding to a more complex coil. It is therefore important to note that the "mid-point" of the transducer may have a multi-dimensional form. Further, the mid-point may be a function of both the primary and the secondary circuit in the transducer, for example due to the fact that the secondary circuit is loaded low-ohmically whereby the secondary current likewise influences the eddy current.

By the term DIFFERENCE is meant, for example, the difference or quotient between two functions or signals.

SUMMARY OF THE INVENTION

The invention may be described as a method and a device for testing and/or measuring of electrically conductive test objects with respect to imperfections in or on the test object. The invention involves the use of at least one transducer, for example a coil or the like, which is fed with electrical signals, for example current, of various frequency contents, for example several currents or voltages of different frequencies simultaneously superposed on each other, so that currents, for example eddy currents, are induced in the test object, for example on the surface thereof, whereby the transducer is influenced by the test object via the inductive coupling-/interaction between the transducer and the test object, and that information, for example signals, directly or indirectly originating from the transducer (with the test object), is used for detection of an imperfection in the test object, for example by way of a vector transformation method or the like, the invention being characterized in that the transducer is designed and supplied in such a way that a complete or partial suppression is obtained of at least one of the undesired effects, for example signals, which directly or indirectly may be caused by the difference in the depth of penetration of the currents which are generated, for example induced, in the test object. This embodiment and/or this mode of supply aim(s) at giving the transducer different properties at different frequencies so that, for example, the midpoint (MPKT) of the at least one transducer is different in some respect for at least two different frequencies or complexes of frequencies. Somewhat simplified, this could be described such that the transducer apparently fictitiously assumes different positions and contours for different frequencies with respect to the connection between the transducer and the test object.

By making the difference between at least two of the mid-points of the transducer (later designated $\Delta$MPKT) as great as the corresponding difference in depth (later designated $\Delta$DJ) of the high- and low-frequency sum currents several advantages result. One of these advantages is that the LO-dependence of the measurement method can be efficiently suppressed because the LO-functions (at the frequencies in question) follow substantially similar functions whereby the LO-dependence can be balanced or compensated for by combining, for example, functions of different frequency origins.

BRIEF DESCRIPTION OF THE DRAWINGS

The invention will now be described, by way of example, with reference to the accompanying drawings which are schematic and are not drawn to scale or in a realistic manner. In the drawings.

DESCRIPTION OF THE PREFERRED EMBODIMENTS

Figure 1:
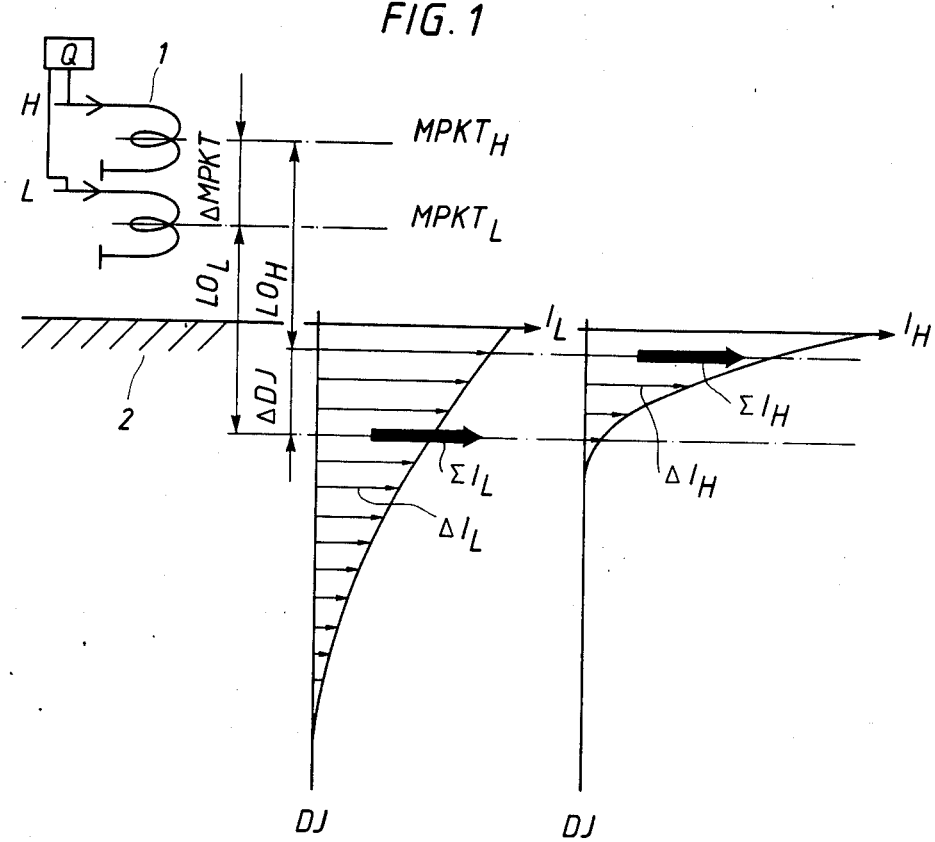
FIG. 1 shows a two-coil transducer above a surface of a test object and indicates the quantities referred to in the specification and, on the right, the distribution of induced current at low- and high-frequencies within the test object as a function of depth below the surface.

A transducer 1 consists, in the arrangement shown in FIG. 1, of two coils which are supplied with currents of high- and low-frequency (H and L, respectively) from a power supply Q. The mid-point of the high frequency coil is positioned at a level $MPKT_H$ and in a corresponding manner the mid-point of the low frequency coil is positioned at a level $MPKT_L$. The transducer is located adjacent a surface of a test object 2, and the current penetration in the object 2 will be as indicated to the right in FIG. 1. As will be seen, the current intensity of each of the low- and high-frequencies decreases with increasing depth (DJ). The difference in depths ($\Delta$DJ) of the sum currents ($\Sigma$I) and the consequences that this involves are of great interest in this connection. The partial currents are marked $\Delta I_L$ and $\Delta I_H$ and should be understood to be the actual current at the respective depth.

It will be appreciated that this arrangement is similar to that described in Swedish patent application No. 8400698-0 entitled "Dynamic Transformation", except for the fact that the transducer is supplied differently at different frequencies.

By designing and supplying the transducer so that $\Delta DJ = \Delta MPKT$, $LO_H$ will be equal to $LO_L$, whereby the LO-dependence at the frequencies H and L will substantially follow similar functions (possibly by means of weighting, etc.), which makes it possible to suppress the LO-dependence measured between the frequencies. Thus, without the need for advanced electronic equipment an undesired influence of—as in this case—LO can be efficiently suppressed in or by means of the transducer itself.

Figure 3:
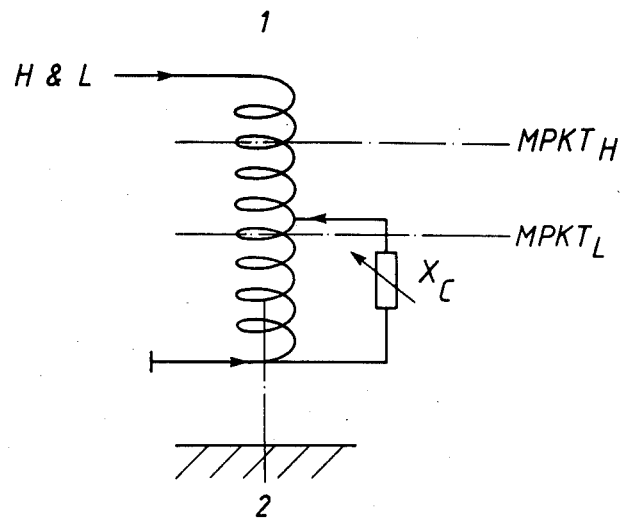
FIGS. 3 and 4 show schematically other arrangements which can be used for a transducer to be employed in the present invention.
Figure 4:
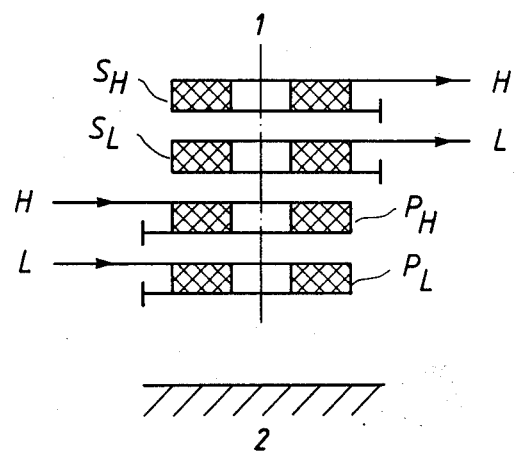

As shown in FIG. 1, the transducer may consist of two coils which are supplied with currents of different frequencies, for example H and L, but the transducer can also be designed, for example, as is shown in FIGS. 3 and 4. In FIG. 4, which represents the cross-section of the transducer, $P_H$ and $P_L$ represent the two coils in FIG. 1, whereas $S_H$ and $S_L$ are separate secondary coils. P and S here represent Primary and Secondary. The transducer may, of course, consist of a plurality of conceivable variants in addition to the types described here.

FIG. 3 shows a transducer consisting of a coil 1 and a reactance, for example a capacitor $X_C$, which is connected across part of the coil 1 while at the same time the coil is supplied with two frequencies (H & L) simultaneously. Since the high frequency component involves a lower impedance in the capacitor than the low frequency component, a larger part of the high-frequency current component will bypass the lower portion of the coil than will be the case with the low-frequency component, whereby the mid-point of the transducer for the high-frequency component ($MPKT_H$) will have a different position in the transducer than the mid-point of the low-frequency component ($MPKT_L$) as shown in FIG. 3. Thus, in principle, it can be seen that the transducer in FIG. 3 corresponds to the two coil transducer shown in FIG. 1.

If, for example, the reactance $X_C$ is made variable, the effective distance between $MPKT_H$ and $MPKT_L$ may be varied. If, in addition, the magnitude of $X_C$ is controlled, for example, with the aid of a control signal, the distance setting between the high- and low-frequency mid-points of the transducer can be remote-controlled in a simple manner.

Figure 2:
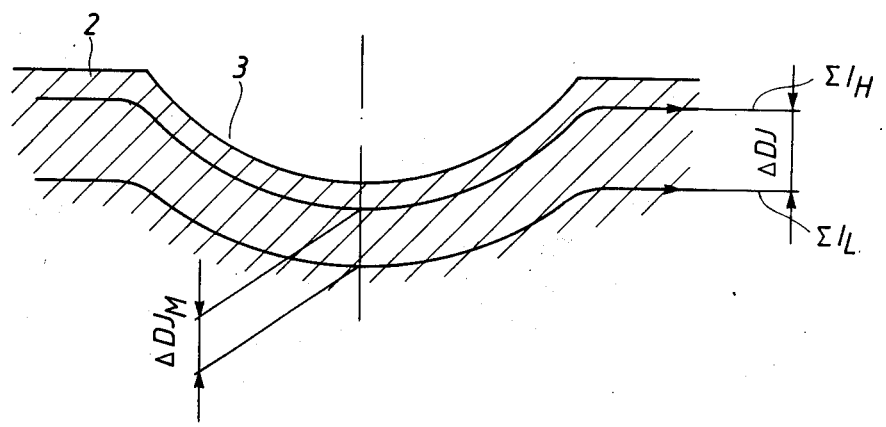
FIG. 2 shows the effect of a surface blemish in a test object on the induced sum currents flowing in the object.

FIG. 2 schematically shows a cross-section of an oscillation mark 3 (OSCM) on the surface of, for example, a billet 2. FIG. 2 shows also the current paths of the sum currents $\Sigma I_H$ and $\Sigma I_L$, and it can be seen that the sum current paths are somewhat closer directly below the mark 3 than they are on either side of the OSCM 3. In addition to the fact that the mutual positions of the current paths may vary, their appearance in other respects may also be different. However, the most important thing is perhaps that $\Delta DJ_M \neq \Delta DJ$ at a deeper OSCM.

In the same way as the LO-dependence can be suppressed by means of the invention, oscillation marks can be suppressed by a suitable choice of transducer design and/or supply. For example, the difference between the mid-points may be adapted to a mean value of $\Delta DJ$ and $\Delta DJ_M$, whereby any unwanted influence of oscillation marks can be suppressed—if not completely then sufficiently to permit a significantly improved signal to noise ratio to be obtained. The suppression can be even better if the mid-point of the transducer is multidimensional in nature and substantially corresponds to the contour and shape of the OSCM.

For example, by continuously varying the shape and position of the mid-point and simultaneously studying the S/N ratio, it is possible to choose the type of shape and/or position which provides the best S/N. This can be carried out, for example, with the aid of a computer and adjustments can be made automatically when required. In this way, an automatic adaptation and optimizing in relation to the surface structure of the test object can be obtained.

As will be clear, the invention is based on the fact that the so-called mid-points of the transducer are at different positions for different frequencies, so that the difference between the depth of current penetration at the different frequencies into the test object is largely compensated for. In this way it is possible to suppress undesired signals, caused by the difference in eddy current propagation. Since, for example, cracks have an influence on the eddy current propagation which is different from, for example, a surface depression, cracks can be detected in the presence of depressions.

The invention of course also comprises those cases where combinations of the mid-points of different frequencies are combined so as to obtain the desired suppression.

In the Figures, the mid-points of the transducers have been represented as chain lines indicating planes at different levels above the surface of the object 2, and the existence of such planes is fully sufficient for many measuring applications. However, it is important to realise that the mid-points may also follow, for example, three-dimensional shapes in order the better to compensate for a multi-dimensional arbitrary change of the surface structure of the test object 2.

The concept of a "mid-point" of the transducer for a respective high- and low-frequency component has been introduced in the absence of a better designation. Since it is not only a question of a point, a term such as "surface of application", may perhaps be a better designation.

In those cases where the distance between the transducer and the test object is large relative to $\Delta DJ$, the LO-functions are substantially similar, as is readily apparent from FIG. 1, whereby the undesired effects, caused by the difference in penetration depth ($\Delta DJ$), are moderate even if $\Delta MPKT=0$. Unfortunately, however, the sensitivity to defects and so on is also drastically reduced with an increasing LO-distance, which makes it unrealistic to operate with large LO-distances. The need of an increased sensitivity to, for example, cracks, that is, the fact the the LO-distance is relatively small, also heightens the need for the present invention. Another important consequence of the invention is the extended LO operating range which is made available by its use.

The invention can be varied in many ways within the scope of the appended claims.

What is claimed is:

1. A method for testing an electrically conductive object for the presence of imperfections therein, comprising:
    moving at least one transducer over the surface of said object at a predetermined distance therefrom;
    exciting said at least one transducer with electrical signals having at least two different frequencies to induce corresponding different electrical eddy currents at different depths in the object and separated by a distance $\Delta DJ$ and the at least one transducer having a different effective midpoint for each of said at least two different frequencies with a separation between the effective midpoints of $\Delta MPKT$;
    sensing said different electrical eddy currents with said at least one transducer and providing transducer output signals representative thereof; and
    varying the excitation of said at least one transducer such that $\Delta DJ$ substantially equals $\Delta MPKT$ to compensate for the difference in the depth of penetration of the electrical eddy currents induced in said object.

2. A method according to claim 1 wherein the step of varying the excitation changes the effective mid-point of said at least one transducer.

3. The method according to claim 1 wherein the step of varying the excitation results in a difference between the effective mid-points of two of said at least one transducer substantially corresponding to the difference in depth between the corresponding eddy currents induced by the different excitation frequencies.

4. The method according to claim 2 wherein the step of varying the excitation includes connecting a reactive element across a part of only one of said at least one transducer for obtaining different effective mid-points of said at least one transducer for excitation signals of different frequencies.

5. A device for testing an electrically conductive object for the presence of imperfections therein, comprising:
    at least one transducer adapted to be moved over the surface of said object at a given distance from the surface thereof:
    said at least one transducer being adapted to be excited with electrical signals having at least two different frequencies to induce corresponding different electrical eddy currents at different depths in the object and separated by a distance $\Delta DJ$ and the at least one transducer having a different effective midpoint for each of said at least two different frequencies with a separation between the effective mid-point of $\Delta MPKT$;
    said at least one transducer sensing said different electrical eddy currents and providing output signals representative thereof; and means for altering the excitation of said at least one transducer such that $\Delta DJ$ substantially equals $\Delta MPKT$ to compensate for the difference in depth of penetration of said electrical eddy currents induced in said object.

6. A device according to claim 5 wherein said means for altering the excitation of said at least one transducer changes the effective mid-point of said at least one transducer.

7. A device according to claim 6, in which the at least one transducer consists of differently positioned coils with respect to the surface of said object.

8. A device according to claim 6, further comprising at least one reactive element connected across a part only of one of said at least one transducer for obtaining different mid-points for the excitation signals of different frequencies.

9. A device according to claim 8, in which said at least one transducer includes a transducer coil divided into upper and lower parts and a capacitor connected in parallel across the lower part of the transducer coil.

10. A device according to claim 6, in which the shape of the at least one transducer is adapted for suppression of a certain type of surface change of the object.

11. A device according to claim 10 wherein said excitation altering means includes means for adjusting the effective mid-point of said at least one transducer such that $\Delta DJ$ substantially equals $\Delta MPKT$.

12. A device according to claim 8, in which the at least one reactive element is a variable reactance element.

13. A device according to claim 6, in which the mid-point of the at least one transducer is of a multi-dimensional nature.

14. The device according to claim 6, wherein the difference between two effective mid-points of two of said at least one transducer substantially corresponds to the difference in depth between the corresponding sum currents induced by the different excitation frequencies.

15. The device according to claim 6, wherein the difference between two effective mid-points of two of said at least one transducer substantially corresponds to the difference in depth between the corresponding sum currents induced by the different excitation frequencies.

* * * * *